(12) United States Patent
Hadden

(10) Patent No.: US 6,482,389 B1
(45) Date of Patent: Nov. 19, 2002

(54) METHOD TO DIAGNOSE AND MONITOR CELLULAR IMMUNE DEFICIENCIES

(75) Inventor: John W. Hadden, Cold Spring Harbor, NY (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/529,566

(22) PCT Filed: Oct. 16, 1998

(86) PCT No.: PCT/US98/21915

§ 371 (c)(1),
(2), (4) Date: Jun. 2, 2000

(87) PCT Pub. No.: WO99/20788

PCT Pub. Date: Apr. 29, 1999

Related U.S. Application Data

(60) Provisional application No. 60/062,322, filed on Oct. 17, 1997.

(51) Int. Cl.[7] .............................................. A61K 49/00
(52) U.S. Cl. ............................ 424/9.2; 424/9.1; 435/4
(58) Field of Search ................................ 435/4; 424/9.1, 424/9.2

(56) References Cited

U.S. PATENT DOCUMENTS

| | | |
|---|---|---|
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,879,219 A | 11/1989 | Wands et al. |
| 5,011,771 A | 4/1991 | Bellet et al. |
| 5,281,521 A | 1/1994 | Trojanowski et al. |
| 5,632,983 A | 5/1997 | Hadden |

OTHER PUBLICATIONS

Stites et al (eds), *Basic and Clinical Immunology* (8th Edition), Appleton & Lange, Norwalk, CT (1994)).

Hadden et al. *Interleukins and Contrasuppression Induce Immune Regression of Head and Neck Cancer*, Int. Arch. Otolaryngol., 120:395–403, 1994).

Mishell and Shiigi (eds), *Selected Methods in Cellular Immunology*, W.H. Freeman and Co., New York (1980).

Sambrook et al, *Molecular Cloning: A Laboratory Manual*, Cold Spring Harbor, New York, 1989.

Webb et al. *Mitogen–Induced Human Lymphocyte Activation in Serum–Free Medium*[1,]*Clinical Immunology and Immunopathyology 1*, 304–310 (1973).

Gillis et al *T Cell Growth Factor: Parameters of Production and a Quantitive Microassay for Activity*, J. Immunol., 120:2027–2032, 1978.

Primary Examiner—Patrick J. Nolan
(74) Attorney, Agent, or Firm—Kohn & Associates

(57) ABSTRACT

A method and kit for determining candidates for immunotherapy, for monitoring the effect of immunotherapy and analysis of cell mediated immunity functionality in a patient who needs immunotherapy is provided. The method includes performing two intracutaneous skin tests and reading the skin test after twenty-four hours. One skin test is the administration of a mitogen such as phytohemagglutinin (PHA), concanavalin A (ConA), pokeweed antigen (PWA) and other mitogens as known in the art. The PHA skin test responses reflect the ability of the T-lymphocytes which are present to react to PHA and to release cytokines like IL-2 and induce a monocyte/macrophage infiltration leading to the DTH dermal reaction which is observed in the skin test characteristic of the afferent limb response of the immune system. The NCM (mitogen-stimulated natural cytokine mixture) skin test reflects the ability of preformed T-cell cytokines to induce the monocyte/macrophage accumulation characteristic of the efferent limb response.

6 Claims, 2 Drawing Sheets

US 6,482,389 B1

METHOD TO DIAGNOSE AND MONITOR CELLULAR IMMUNE DEFICIENCIES

This application is a 35 USC 371 of PCT/US98/2195, filed Oct. 16, 1998, which claims benefit under 35 USC 119(e) to U.S. provisional application 60/062,322, filed Oct. 17, 1997.

BACKGROUND OF THE INVENTION

1. Field of the Invention

A method and kit to monitor and for diagnosis of cellular immune deficiencies.

2. Description of Related Art

A variety of clinical tests have been used to evaluate cellular immune responses in diseases involving congenital or acquired cellular immune deficiency (see in general Stites et al. (eds), Basic and Clinical Immunology (8th Edition), Appleton & Lange, Norwalk, Conn. (1994)). Primary cellular immune deficiency such as DiGeorge Syndrome is associated with the lack of a thymus and thus T-lymphocytes in blood and tissues. Secondary cellular immune deficiencies occur in a variety of conditions (see Table I), perhaps most notably in cancer and human immunodeficiency virus (HIV) infections. In these diseases, impairment of T-lymphocyte functions (proliferation, cytokine production, cytotoxicity, help and suppression) are often manifest early and followed by a loss of T-lymphocytes in blood (lymphocytopenia) and lymphoid tissues. Often, monocyte/macrophage defects occur which may contribute to impairment of cellular immunity (CMI) also referred to as delayed-type hypersensitivity (DTH).

DTH is frequently tested clinically with the use of skin tests to recall antigens such as purified protein derivative (PPD), tetanus toxoid, candida and other antigens. These tests are not generally standardized. One test device, the Merieux Multitest device, has been employed; however, it is expensive (>$90/test) and insensitive and prone to false negative reaction. Perhaps the most useful test historically, particularly in cancer, has been primary sensitization with a new antigen like dinitrochlorobenzene (DNCB), followed by a challenge. The DNCB skin test has been useful to predict survival in patients with human cancer i.e. patients with a good response to DNCB will live longer and have better survival rates with conventional therapy then those who have a poor response. It is, however, difficult to perform and there are concerns regarding possible toxicity, and cross-sensitizing (Stites, et al, ibid at page 196) and is thus seldom used.

T-lymphocyte (CD3, CD11) and subsets (CD4, CD8) counts using cytofluorometry (FACS) are now performed frequently on patients with HIV infection and are considered to be an important prognostic predictor of the outcome of this disease. FACS analyses of T-lymphocyte and subsets are expensive tests and generally only available in the industrialized countries.

Historically, physicians have performed routinely a complete blood count (CBC) and differential. With these data the white blood cell count (WBC) and the percent of lymphocytes are determined; however, in general, the WBC and percent lymphocyte are not multiplied to yield a lymphocyte count (normally around 2000 mm$^3$). Further, approximately 20% of circulating lymphocytes are B-lymphocytes and these values have been determined to vary little throughout life and during various disease. Thus, physicians are generally unaware that lymphocyte counts of <1500 mm$^3$ reflect mainly T-lymphocytopenia approaching clinical significance.

Where analyzed, T-lymphocytopenia as occurs in cancer, cancer therapy, irradiation, and HIV infection generally reflects greater early losses of CD4 than CD8 cells. Thus, one can determine a lymphocyte count and infer with a great degree of accuracy that if it is significantly low (i.e. <1500 mm$^3$) then T-lymphocytopenia is present and cellular immunity may be impaired.

A variety of in vitro tests of T-lymphocyte function have been developed including lymphoproliferative responses to mitogens like phytohemagglutinin (PHA) or Concanavalin A (Con A), interleukin (IL) production like IL-2 and gamma interferon (IFN-$\gamma$), cytotoxicity for target cells, etc. These tests are expensive, cumbersome, and performed only at academic centers where appropriate research laboratories are present.

Clinical medicine needs not only new approaches to the diagnosis of cellular immune deficiency but also to monitor the effect of immunotherapy. Historically, natural killer (NK) cells have been employed to monitor the effect of recombinant interferon alpha (rIFN-$\alpha$) therapy, yet in fact clinical responses have not correlated with NK cell number or activity. T-lymphocyte counts have responded to intravenous therapy with high dose rIL-2; however the response is little or not at all with subcutaneous therapy with low doses of rIL-2. Thus, new approaches are needed for the diagnosis and monitoring of CMI in human patients with cancer and other diseases in which cellular immune deficiencies are common.

The use of a natural cytokine mixture (NCM) has proven effective in the treatment of cellular immune deficiency relating to age and stress (U.S. Pat. No. 5,632,983).

The clinical application of this NCM in the immunotherapy of four patients with squamous cell head and neck cancer (H&N SCC) induced significant immune regressions in three of four patients (Hadden et al. "Interleukins and Contrasuppression Induce Immune Regression of Head and Neck Cancer" Int. Arch. Otolaryngol., 120:395–403, 1994). In this study, a DTH intracutaneous skin test was performed. Three patients who were lymphocytopenic responded to NCM therapy with increased T-lymphocyte counts, including the skin test negative patient; thus, the skin test did not appear to predict the immunorestorative response to NCM.

It would be useful to effectively analyze DTH in the patient with cellular immune deficiency and to monitor the effect of immunotherapy designed to correct this deficiency.

SUMMARY OF THE INVENTION

According to the present invention, a method and kit for determining candidates for immunotherapy, for monitoring the effect of immunotherapy and analysis of cell mediated immunity functionality in a patient is provided. The method includes performing two intracutaneous skin tests and reading the skin test after twenty-four hours. One skin test is the administration of a mitogen such as phytohemagglutinin (PHA), concanavalin A (ConA), pokeweed antigen (PWA) and other mitogens as known in the art. The PHA skin test responses reflects the ability of the T-lymphocytes which are present to react to PHA and to release cytokines like IL-2 and induce a monocyte/macrophage infiltration leading to the DTH dermal reaction which is observed in the skin test characteristic of the afferent limb response of the immune system. The NCM (mitogen- stimulated natural cytokine mixture) skin test reflects the ability of preformed T-cell cytokines to induce the monocyte/macrophage accumulation characteristic of the efferent limb response.

The kit contains the appropriate mitogen and NCM to be used in the skin tests.

In other words, the present invention provides a method to monitor patients with cellular immune deficiency by the steps of determining the result of intracutaneous skin tests with a mitogen such as PHA and with natural cytokine mixture (NCM) and the result of blood lymphocyte counts (with or without T-lymphocyte and subset enumeration) to yield a composite "three-dimensional view" of CMI including T-lymphocyte number and function (afferent limb) and cytokine production and action on monocytes and macrophages (efferent limb)

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
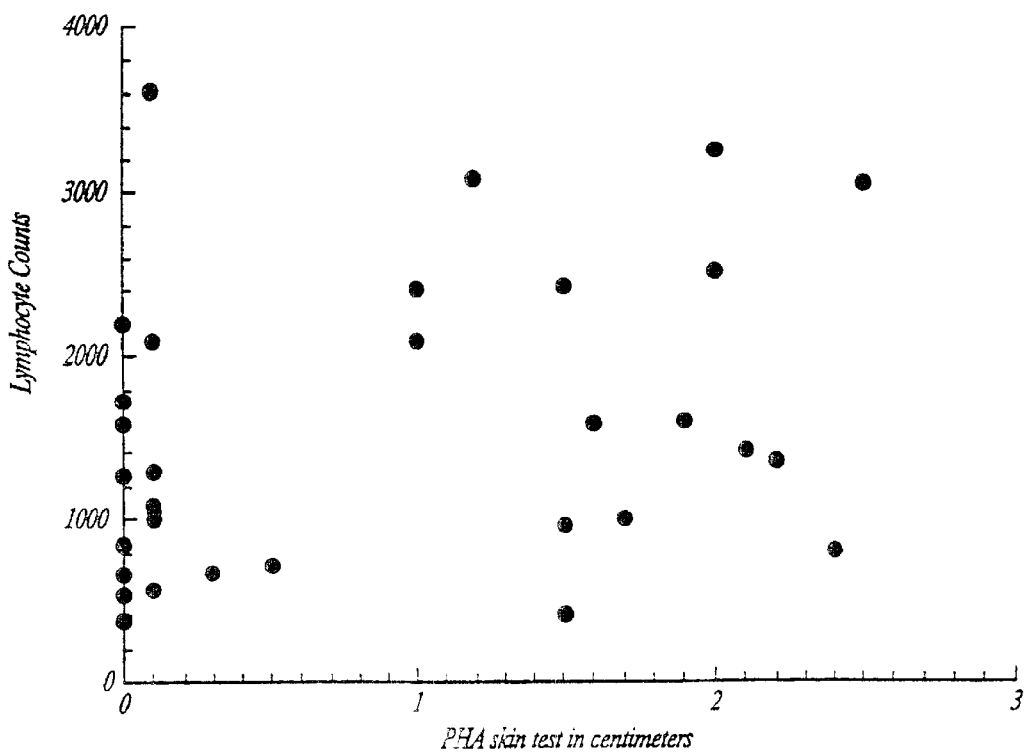
FIG. 1 is a graph showing the correlation between lymphocyte count and PHA skin test response in cancer patients.

The present invention provides a method and kit for determining candidates for immunotherapy and for monitoring the effect of immunotherapy in a patient undergoing immunotherapy (see Table 1). Patients who need to be selected as candidates for immunotherapy for example are patients who have cancer. Patients who need to be monitored for example are patients who are undergoing immunotherapy for cancer. It is useful to know if the patient is responding or has the potential for responding no matter the white blood cell count. Additionally, the method of the present invention allows the selection of patients who are good candidates for immunotherapy amount those patients who need immunotherapy.

The method includes performing two intracutaneous skin tests and reading the skin test after twenty-four hours. One skin test is the administration of a mitogen such as phytohemagglutinin (PHA), concanavalin A (ConA), pokeweed antigen (PWA) and other mitogens as known in the art. As shown in the exemplar herein, when PHA is used the dose administered is between the range of 0.5 to 1.0 $\mu$g. As shown in Example 2 herein, there is a correlation with responsiveness in the skin tests to immunotherapy response, particularly to immunotherapy with NCM.

The PHA skin test responses reflect the ability of the T-lymphocytes which are present, to react to PHA and to release cytokines like IL-2, IFN K, etc. and induce a monocyte/macrophage infiltration leading to the DTH dermal reaction which is observed in the skin test characteristic of the afferent limb response of the immune system. The NCM (mitogen-stimulated natural cytokine mixture) skin test reflects the ability of preformed T-cell cytokines to induce the monocyte/macrophage accumulation characteristic of the efferent limb response. The two responses allow the determination of whether the afferent or efferent or both limbs of the immune response are affected and can then be correlated with T-cell number. In other words, the functionality of the T-cells present can be determined by this method and it will have an effect on the outcome and design of immunotherapy. The present invention allows the monitoring during immunotherapy for changes to determine if the course of treatment is having an effect and in which direction. It further allows for monitoring that the immunotherapy is not causing changes in the responsiveness of the T-cells present in the patient. Further, by knowing whether both the efferent and afferent limbs of the immune system are functional, good candidates for immunotherapy can be selected.

The kit contains the appropriate mitogen and NCM at the required concentrations to be used in the skin tests. Additionally, the kit will contain the materials including syringes and needles to administer the skin test as well as control solutions that do not contain the mitogen or NCM.

The method of the present invention and kit also provide an analysis of the functionality of cell mediated immunity in a patient needing such an analysis. As described herein above, two intracutaneous skin tests are administered and read after twenty-four hours. The two skin tests are the NDM and mitogen skin tests. In addition a white blood cell count with the percent lymphocytes determined is also performed. The results of a lymphocyte count of <1500 mm$^3$ indicate a T- lymphocytopenia. The further analysis then allows the determination of how the T-cells that are present are functioning, that is, are only the afferent or efferent or both limbs of the immune system functional. Patients who respond positively to the PHA intracutaneous skin tests have a functional afferent immune system response and patients who respond positively to the NCM intracutaneous skin tests have a functional efferent immune system response such that the functionality of the T-cells that are present can be determined.

In summary, the present invention provides a method to monitor patients with cellular immune deficiency by the steps of determining the result of intracutaneous skin tests with a mitogen such as PHA and with natural cytokine mixture (NCM) and the result of blood lymphocyte counts (with or without T-lymphocyte and subset enumeration) to yield a composite "three-dimensional view" of CMI including T-lymphocyte number and function (afferent limb) and cytokine production and action on monocytes and macrophages (efferent limb). The methods used with and the utility of the present invention can be shown by the following non-limiting examples and accompanying FIGS.

EXAMPLES

Methods

General methods in immunology: Standard methods in immunology known in the art and not specifically described are generally followed as in Stites et al. (eds), Basic and Clinical Immunology (8th Edition), Appleton & Lange, Norwalk, CT (1994) and Mishell and Shiigi (eds), Selected Methods in Cellular Immunology, W. H. Freeman and Co., New York (1980). Immunoassays: In general, ELISAs are one immunoassays employed to assess a specimen as needed. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, N.Y., 1989

Skin Tests

Intracutaneous skin tests are performed and evaluated as is generally known in the art. Briefly, sterile test solutions are prepared and administer generally using 25- or 27-gauge needles. The largest dimensions of both erythema and induration are measured with a ruler, in the method of the present invention at 24 hours The inflammatory infiltrate that accumulates at the site and accompanying edema result in the induration of the skin and the diameter of this reaction an index of the response. Induration of 5 mm or more in diameter is the generally accepted criterion of a positive response, strong positive (major) responses can be grater than 1 centimeter. In general a negative reaction will provide a response similar to the control (no antigen) site.

Preparation of natural cytokine mixture (NCM)

The buffy coat white cells of human blood from multiple HIV-negative hepatitis virus-negative donors is collected. In an alternative embodiment, animals are the cell source for veterinary uses. The cells from the donors are pooled and layered on ficoll hypaque gradients (Pharmacia) to yield lymphocytes free of neutrophils and erythrocytes. (U.S. Pat. Nos. 4,390,623 and 4,448,879) Alternative methods are used that would result in the same starting lymphocyte population as are known in the art.

The lymphocytes are washed and distributed in X vivo-10 media (Whittaker Bioproducts) to flasks (MicroCELLector™ T-25 Cell Culture Flasks) in which are immobilized stimulants, i.e. mitogens, and in a preferred embodiment of the present invention PHA. However, Cibcabavakub A (ConA), pokeweed antigen (PWA) or OKT-3 can be used. Alternatively, X vivo-15 and X vivo-20 media can be used. The immobilization process for the stimulants is as described by the manufacturer for immobilizing various substances for panning procedures, i.e. separating cells, in the flasks.

The cells are incubated for 24-48 hours in X vivo-10 media with 80 $\mu$/ml ciprofloxacin (Miles Lab) at 37° in a $CO_2$/air incubator. Alternatively, RPMI 1640 media is used (Webb et al. 1973). Generally the HSA is used at 0.1 to 0.5% (weight by volume). Following incubation the supernatants are poured off and collected. Human serum albumin (HSA) can be added to stabilize further the interleukins. The supernatants are stored at 4° C. to −70° C.

Characterization of Supernatants

The pooled supernatants are characterized by measuring the cytokine content by bioassay for IL-2 and ELISAs for the remaining interleukins IL-1–IL-15, CSFs, TNFs, and IFNs. Specifically, the following assays and kits are used in a preferred embodiment:INF-$\gamma$ ELISA (ENDOGEN), IL-1, IL-2, IL-3, IL-4, IL-6, IL-7, IL-8, GM-CSF, G-CSF and TNF-$\alpha$ ELISAs (R&D Systems). The IL-2 bioassay is by the method of Gillis et al. (Gillis et al. "T Cell Growth Factor: Parameters of Production and a Quantitive Microassay for Activity" *J. Immunol.*, 120:2027–2032, 1978) and is expressed as units/ml compared to a known standard of IL-2 (Schiapparelli Biosystems, Inc., Fairfield, N.J.). Sterility is tested by culture in thioglycolate broth and endotoxin measured by limulus lysate assay as is known in the art.

Standardization of Supernatant for Cytokine Content

Each supernatant is standardized for IL-2 content either by concentration or amount administered. In general for skin tests, the NCM is standardized to have an equivalence of 15 Units of IL-2 by bioassay in 0.1 ml of the supernatant.

Removal of Contaminants from Supernatant

DNA and virus exclusion, when used, employ such techniques as ultrafiltration, column chromatography, virasol, ethanol fractionation, polyethylene glycol/bentonite precipitation, gamma irradiation, and/or solvent/detergent treatment as has been used for intravenous gamma globulin and monoclonal antibodies (e.g. IGIV News Update brochure).

Example 1

Skin tests with PHA (0.5 or 1.0 $\mu$g) were performed in ten patients with H&N SCC and twenty-three Taxol-treated patients with breast cancer and nine healthy controls. Sixty-seven percent of cancer patients (14/21) did not respond to the 0.5 $\mu$g dose of PHA and had mean lymphocyte counts of 1257±167. Forty-seven percent of the cancer patients (15/33) did not respond to the 1.0 $\mu$g dose of PHA and had mean lymphocyte counts of 1383±214. The responders (7/12 & 18/33) had lymphocytes, respectively, of 2095±354 and 1755±219. All of the controls responded and had a mean lymphocyte count of 2107±285. Failure to respond to the PHA, particularly the 0.5 $\mu$g dose, is thus common in the cancer patients and reflects published anergy figures for DNCB. While patients anergic to PHA show significantly lower lymphocyte counts, the correlation of the two (FIG. 1) is not high, reflecting the fact that the defects of anergy and lymphocytopenia are related but are not obviously cause and effect.

Example 2

Figure 2:
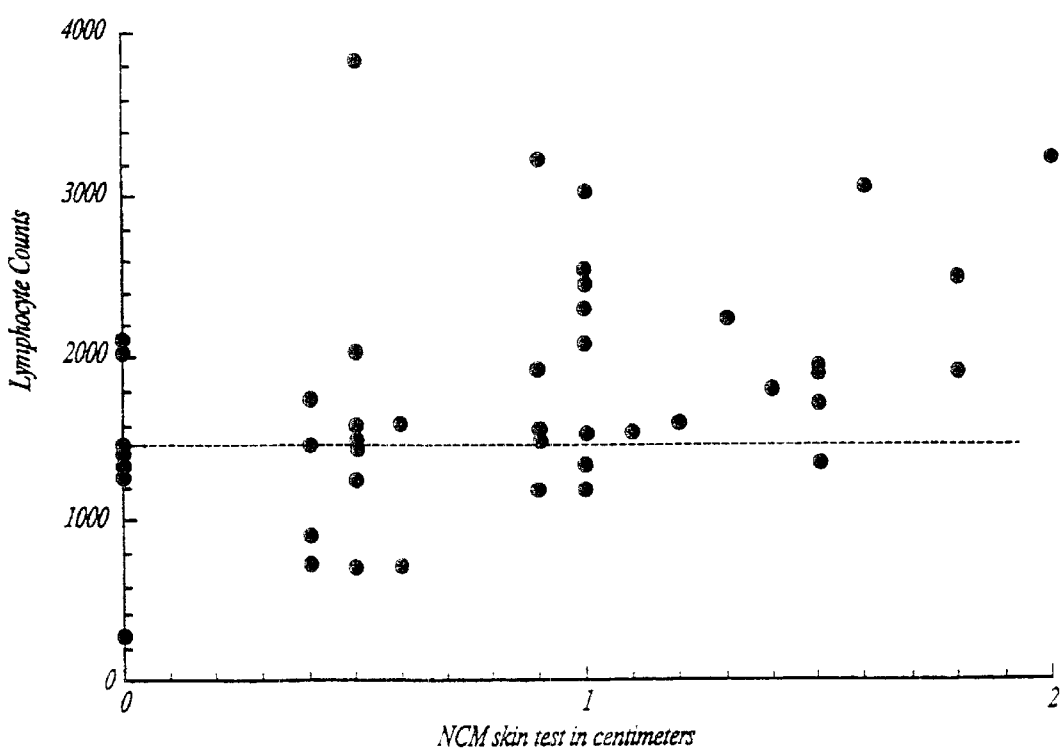
FIG. 2 is a graph showing the correlation between lymphocyte count and NCM skin test response in patients with squamous cell head and neck cancer (H&N SCC)
Figure 4:
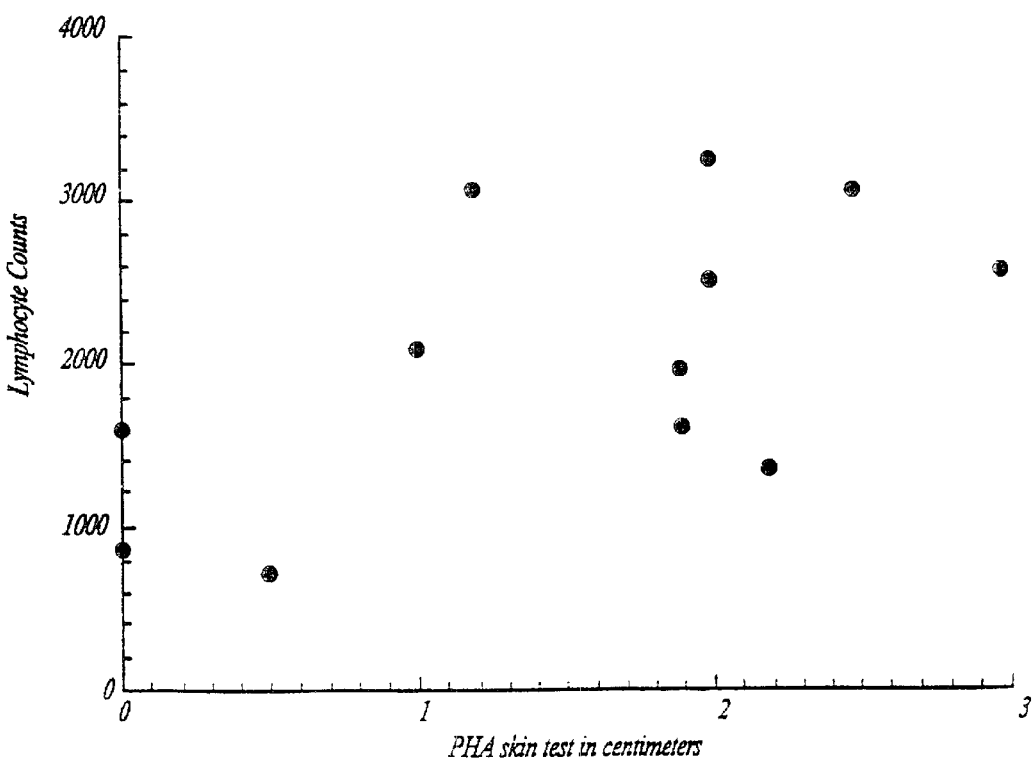
FIG. 4 is a graph showing the correlation between lymphocyte count and PHA skin test response in patients with squamous cell head and neck cancer (H&N SCC).

H&N SCC patients were analyzed for PHA and NCM skin tests and lymphocyte counts and little or no correlations were observed (FIGS. 2, 4). These data indicate that each test is looking at a different component of the CMI/DTH defects in H&N SC cancer as would be expected:
1) T-lymphocyte counts reflect T-lymphocyte number and indirectly the pool size;
2) PHA skin test responses reflects the ability of these T-lymphocytes which are present to react to PHA and to release cytokines like IL-2, IFN K, etc. and induce a monocyte/macrophage infiltration leading to the DTH dermal reaction, and
3) the NCM (mitogen-stimulated natural cytokine mixture) reflects the ability of preformed T-cell cytokines to induce the monocyte/macrophage accumulation characteristic of the efferent limb response.

Thirty-three patients with locally advanced H&N SC cancers were skin tested with intracutaneous i.e. injections of NCM prior to immunotherapy with NCM in the immunotherapy strategy (Hadden et al., 1994 ibid). Twenty-five patients were NCM-positive and eight were negative to the NCM skin test read at 24 hours. Of the twenty-five, fifteen NCM positive patients had major clinical responses and eleven had minor or no response; of the eight NCM negative patients, none had major responses (TABLE 2).

Figure 3:
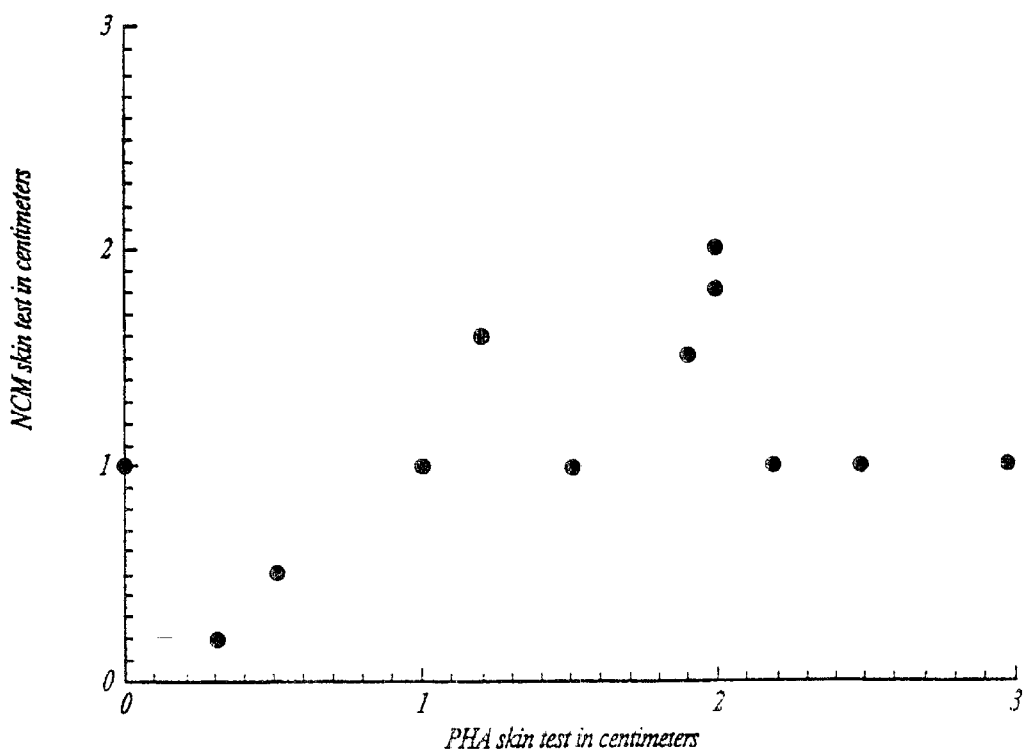
FIG. 3 is a graph showing the correlation between PHA and NCM skin test response in patients with squamous cell head and neck cancer (H&N SCC)

Of the major responders in the NCM+ group, only one recurrence with death (7%) has occurred and of the NCM- group four recurrences with death (50%) had occurred. Thus, the NCM skin test is a significant and reliable predictor of clinical response to this immunotherapy protocol unexpectedly based on previous results. (FIGS. 2–4)

Of the twenty-five NCM+ patients on protocol, eight were lymphocytopenic (<1500 mm$^3$) with a mean count of 1247 ±92. All but one of these patients showed an increase in lymphocytes to a mean of 1866±172 (p<0.01 by paired student T-test). Of the eight NCM negative patients, five were lymphocytopenic (mean 1391±37) and only one showed an increase by Chi square analysis (TABLE 3). Thus, the NCM skin test also predicts the immunorestorative effect of NCM on patients with low lymphocyte counts.

In one patient treated with immunotherapy, NCM has been associated with an increase in the PHA skin test. In the three patients, NCM therapy has been associated with an increase in the NCM skin test. Thus, these parameters reflect the effect of immunotherapy. (FIG. 3)

The advantages of this diagnostic approach are its simplicity and cost making the test widely employable, particularly in office practice, rural settings and nondeveloped countries where more complicated tests are not available or not economically feasible to use. The advantage of this approach in monitoring the impact of immunotherapy is unique in that no test or tests have emerged which can consistently monitor any immunotherapy. The combination of these three tests of the present invention therefore are useful for monitoring immunotherapies such as NCM therapy for monitoring which correct T-lymphocyte number and function and/or monocyte/macrophage function.

Throughout this application, various publications, including United States patents, are referenced by author, citation and year and patents by number. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

SECONDARY CELLULAR IMMUNE DEFICIENCY

| | |
|---|---|
| HIV | AGING |
| VIRAL INFECTIONS (TRANSITORY) | ZINC/ ? SELENIUM DEFICIENCY |
| BURNS/TRAUMA/SEPSIS | PROTEIN CALORIE MALNUTRITION |
| CHRONIC INFECTION/PARASITOSIS | IMMUNOTOXICANTS |
| RHEUMATOID ARTHRITIS | IMMUNOSUPPRESSIVE CHEMOTHERAPY |

TABLE 2

| Skin Test Result | Major Response | Minor Response | Total | Chi Square |
|---|---|---|---|---|
| NCM+ | 15 | 10 | 25 | $X^2 = 6.6$ |
| NCM- | 0 | 8 | 8 | $p < 0.01$ |
| Totals | 15 | 18 | 33 | |

TABLE 3

| | | | |
|---|---|---|---|
| 8 | 1 | 9 | $X^2 = 4.0$ |
| 1 | 4 | 5 | $p < 0.05$ |
| 9 | 5 | 14 | |

What is claimed is:

1. A method for selecting candidates for immunotherapy among patients who need immunotherapy including the steps of
    administering an intracutaneous skin test with a mitogen and reading the skin test after twenty-four hours; and
    administering an intracutaneous skin test with a natural cytokine mixture (NCM) and reading the skin test after twenty-four hours;
    wherein patients who respond to both of the intracutaneous skin tests are candidates for immunotherapy.

2. The method as set forth in claim 1 wherein said mitogen is phytohemagglutinin (PHA).

3. The method as set forth in claim 2 wherein the phytohemagglutinin is administered between the range of 0.5 to 1.0 μg.

4. The method as set forth in claim 1 wherein said mitogen is concanavalin A.

5. The method as set forth in claim 1 wherein said mitogen is pokeweed antigen.

6. The method as set forth in claim 1 wherein said NCM is administered at a dose of 0.1 ml which has an equivalence to 15 units of IL-2 by bioassay.

* * * * *